United States Patent
Neice

(10) Patent No.: US 10,702,303 B2
(45) Date of Patent: Jul. 7, 2020

(54) RETREATING STOP ULTRASOUND NEEDLE GUIDE

(71) Applicant: Andrew Neice, Portland, OR (US)

(72) Inventor: Andrew Neice, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 1009 days.

(21) Appl. No.: 14/624,745

(22) Filed: Feb. 18, 2015

(65) Prior Publication Data

US 2016/0242810 A1 Aug. 25, 2016

(51) Int. Cl.
| | |
|---|---|
| *A61B 17/34* | (2006.01) |
| *A61B 8/08* | (2006.01) |
| *A61B 8/00* | (2006.01) |
| *A61M 5/32* | (2006.01) |
| *A61M 5/46* | (2006.01) |

(52) U.S. Cl.
CPC ........ *A61B 17/3403* (2013.01); *A61B 8/0841* (2013.01); *A61B 8/4444* (2013.01); *A61B 17/3401* (2013.01); *A61B 2017/3411* (2013.01); *A61B 2017/3413* (2013.01); *A61M 5/3287* (2013.01); *A61M 5/46* (2013.01)

(58) Field of Classification Search
CPC ... A61M 5/3287; A61M 5/46; A61B 17/3401; A61B 17/3403; A61B 2017/3411; A61B 2017/3413; A61B 8/0841; A61B 8/4444
See application file for complete search history.

(56) References Cited

U.S. PATENT DOCUMENTS

| | | | |
|---|---|---|---|
| 4,469,106 A | 9/1984 | Harui | |
| 5,052,396 A | 10/1991 | Wedel et al. | |
| 5,623,931 A * | 4/1997 | Wung | A61B 17/3403 600/461 |
| 5,941,889 A | 8/1999 | Cermak et al. | |
| 6,361,499 B1 | 3/2002 | Bates et al. | |
| 6,379,307 B1 | 4/2002 | Filly et al. | |
| 8,574,160 B2 | 11/2013 | Gorzitze | |
| 2005/0033315 A1 | 2/2005 | Hankins | |
| 2009/0143684 A1* | 6/2009 | Cermak | A61B 8/0841 600/461 |

(Continued)

OTHER PUBLICATIONS

Ball et al., Randomized, prospective, observational simulation study comparing residents' needle-guided vs free-hand ultrasound techniques for central venous catheter access, British Journal of Anaesthesia, 108 (1), pp. 72-79, 2012.

(Continued)

*Primary Examiner* — Amelie R Gillman

(57) ABSTRACT

Retreating stop ultrasound needle guide systems are disclosed. In one example approach, a needle guide system includes a guiding component which can be positioned at different locations and angles on a mounting component, where the mounting component can be coupled to a distal end of an ultrasound probe. When positioned at the different locations and angles on the mounting component, the guiding component can guide a needle through the skin of a patient at a constant point and when the needle is advanced so that a hub of the needle reaches a stop of the guiding component, a tip of the needle is positioned directly underneath the ultrasound at a pre-selected depth.

15 Claims, 7 Drawing Sheets

(56) References Cited

U.S. PATENT DOCUMENTS

| | | | | |
|---|---|---|---|---|
| 2013/0150714 A1* | 6/2013 | Howlett | ............... | A61B 8/4483 600/439 |
| 2014/0200445 A1* | 7/2014 | Boezaart | ............... | A61M 5/158 600/424 |

OTHER PUBLICATIONS

Blaivas et al., An unseen danger: Frequency of posterior vessel wall penetration by needles during attempts to place internal jugular vein central catheters using ultrasound guidance, Crit Care Med 2009, vol. 37, No. 8, pp. 2345-2349.

Chin et al., Needle Visualization in Ultrasound-Guided Regional Anesthesia: Challenges and Solutions, Regional Anesthesia and Pain Medicine, vol. 33, No. 6, Nov.-Dec. 2008, pp. 532-544.

Choquet et al., The new technological trends in ultrasound-guided regional anesthesia, Current Opinions Anaesthesiology, vol. 26, No. 5, Oct. 2013, pp. 605-612.

Hocking et al., A Review of the Benefits and Pitfalls of Phantoms in Ultrasound-Guided Regional Anesthesia, Regional Anesthesia and Pain Medicine, vol. 36, No. 2, Mar.-Apr. 2011, pp. 162-170.

Barrington, et al., 2012, "Ultrasound-Guided Regional Anesthesia: How Much Practice Do Novices Require Before Achieving Competency in Ultrasound Needle Visualization Using a Cadaver Model," Reg. Anesth. Pain Med., 37(3), pp. 334-339.

Luyet, et al., 2009, "Ultrasound Guided Paravertebral Puncture and Placement of Catheters in Human Cadavers: An Imaging Study," Br. J. Anaesth., 102(4), pp. 534-539.

Wong et al., Real-time ultrasound-guided spinal anesthesia using the SonixGPS(R) needle tracking system: a case report, Can J Anesth, 2013, 60:50-53.

Niazi et al., Real-time ultrasound-guided spinal anesthesia using the SonixGPS ultrasound guidance system: a feasibility study, Acta Anaesthesiol Scand, 2014, 58:875-881.

Tartiere et al., Estimation of the diameter and cross-sectional area of the internal jugular veins in adult patients, Critical Care, vol. 13, No. 6, R197, Dec. 9, 2009, 4 pages.

INRAD(R), AccuPlace(R) Drace Sterotaxic Needle Guide, http://www.inradinc.com/accuplace-drace-stereotaxic-needle-guide/.

Marhofer et al., "Lateral Ultrasound-Guided Paravertebral Blockade: An Anatomical-Based Description of a New Technique," Br. J. Anaesth., 105(4), pp. 526-532.

Hara, et al., 2009, "Ultrasound Guided Thoracic Paravertebral Block in Breast Surgery," Anaesthesia, 64(2), pp. 223-225.

Karmakar, et al., "Ultrasound-Guided Lumbar Plexus Block Through the Acoustic Window of the Lumbar Ultrasound Trident," Br. J. Anaesth., 100(4), pp. 533-537.

Tran et al., 2010, "Single-Operator Real-Time Ultrasound-Guidance to Aim and Insert a Lumbar Epidural Needle," Can. J. Anesth., 57(4), pp. 313-321.

Brinkmann et al., Methodological considerations of ultrasound-guided spinal anesthesia using the Ultrasonix GPSTM needle tracking system, Can J Anesth, 2013, 60:407-408.

Lindgren, 1980, "Ultrasonically Guided Punctures. A Modified Technique," Radiology, 137(1), pp. 235-237.

Read, 1983, "Real-Time Sonographic Needle Biopsy Guide," Am. J. Roentgenol., 140(1), pp. 162-163.

Bard Access Systems, "Product Catalog, Product ID 9002096, 20 Gauge Needle Guide Kit for Site Rite," accessed Feb. 6, 2014, Bard Access Systems Inc., Salt Lake City, UT, http://www.bardaccess.com/ultra-siterite-vision.php.

Denys et al., 1993, "Ultrasound-Assisted Cannulation of the Internal Jugular Vein. A Prospective Comparison to the External Landmark-Guided Technique," Circulation, 87(5), pp. 1557-1562.

Nickalls et al., 1986, "The Width of the Posterior Epidural Space in Obstetric Patients," Anaesthesia, 41(4), pp. 432-433.

Chin et al., 2008, "Needle Visualization in Ultrasound-Guided Regional Anesthesia: Challenges and Solutions," Reg. Anesth. Pain Med., 33(6), pp. 532-544.

Drummond et al., 1980, "Deflection of Spinal Needles by the Bevel," Anaesthesia, 35(9), pp. 854-857.

Whittaker et al., An ultrasound needle insertion guide in a porcine phantom model. Anaesthesia 2013; 68:826-829.

Augoustides et al. A randomized controlled clinical trial of real-time needle-guided ultrasound for internal jugular venous cannulation in a large university anesthesia department. J Cardiothorac Vasc Anesth 2005; 19:310-315.

* cited by examiner

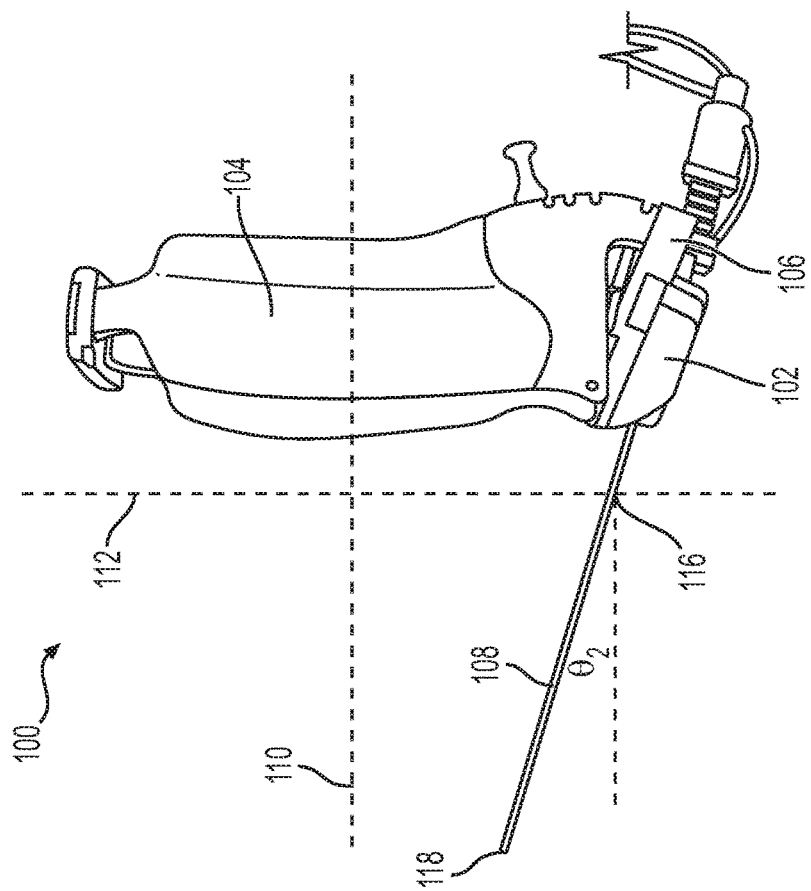
FIG. 1A *(PRIOR ART)*
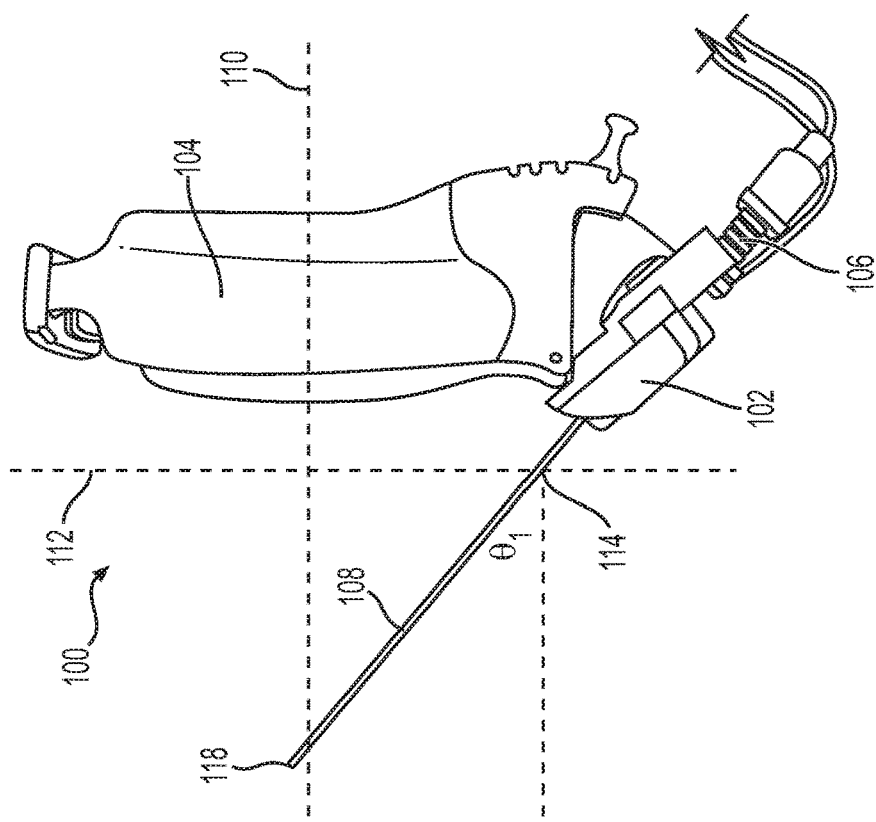
FIG. 1B *(PRIOR ART)*

RETREATING STOP ULTRASOUND NEEDLE GUIDE

FIELD

The present disclosure relates to the field of ultrasound needle guides, and, more specifically, to variable depth ultrasound needle guides.

BACKGROUND

Needle guides may be used to assist in positioning and guidance of needles in a variety of applications such as biopsies, fluid aspirations, and regional anesthesia procedures. In some examples, needle guides may be used together with ultrasound probes in order to guide a needle to a particular position in a patient's tissue. For example, a needle guide may be attached to an ultrasound device to guide a needle during regional anesthesia procedures.

The accuracy, precision, and measurement resolution of needle placement when using needle guides is of importance to the clinician. While some anatomic targets, such as the internal jugular vein, are relatively large and therefore will tolerate guides that lack accuracy, precision, or resolution, procedures that target small structures or are near sensitive tissue are less forgiving.

For most in-plane ultrasound needle guides, the needle can be visualized throughout its trajectory to the target, and the clinician may dynamically correct for any shortcomings in the needle guide, or may choose to not use any needle guide at all. However, for out-of-plane ultrasound needle guide approaches, the needle is not visible until it intersects the plane of the ultrasound image, making needle guides much more useful and the characteristics of the needle guide more important. Additionally, in some in-plane approaches, steep needle trajectories make needle visualization difficult.

Some anesthetic procedures, e.g., paravertebral blocks and lumbar plexus blocks, may be difficult to perform using in-plane ultrasound needle guide techniques due to the desired needle depth, presence of anatomical obstructions, the size/geometry of the ultrasound probe and the altered needle trajectory created, and the steep angle of needle entry, for example. Nevertheless, such anesthetic procedures could benefit from ultrasound guidance.

Some needle guide approaches have changed the selected depth by changing the angle at which the needle penetrates the skin, in a variable-angle style needle guide. However, such needle guides have a limited number of depths and angles available, making them unsuitable for the fine degree of control needed for regional anesthesia. Furthermore, such approaches may not provide any safety mechanism that limits the advancement of the needle, e.g., to reduce inadvertent puncture of vital structures. Further, some approaches provide single use guides which employ differently-shaped clips to achieve different depths, thereby potentially creating confusion during use when selecting the appropriate clip for a desired depth. Because of these issues, many practitioners either do not use an ultrasound probe or 'free-hand' the needle for these procedures. Further, since such approaches are considered to be relatively difficult procedures, they may be performed with less frequency relative to the number of surgeries where patients could obtain benefit from these blocks.

SUMMARY

The present disclosure is directed to a retreating stop ultrasound needle guide system which includes a guiding component which can be positioned at different locations and angles on a mounting component, where the mounting component can be coupled to a distal end of an ultrasound probe. When positioned at the different locations and angles on the mounting component, the guiding component can guide a needle through the skin of a patient at a constant point and when the needle is advanced so that a hub of the needle reaches a stop of the guiding component, a tip of the needle is positioned directly underneath the ultrasound at a pre-selected depth.

Such a retreating stop ultrasound needle guide system may be used in anesthetic procedures, e.g., paravertebral blocks and lumbar plexus blocks, which may be difficult to perform using in-plane ultrasound needle guide techniques due to the desired needle depth, presence of anatomical obstructions, the size/geometry of the ultrasound probe and the altered needle trajectory created, and the steep angle of needle entry, for example.

In particular, such an approach allows a needle to be guided safely into an anatomic space identified via ultrasound while preventing the needle from being advanced too far into vital structures. Such a needle guide system may ensure that the tip of the needle intersects the plane of the ultrasound beam at exactly the desired depth and since the needle penetrates the skin at a constant point in this approach, the guide may show the operator where to penetrate the skin. This can make the angle of entry more accurate than if it was determined only by the needle stop, for example.

In such an approach, an increased number of depths and angles may be used so that increased accuracy, precision, and measurement resolution may be achieved. This approach provides a simple, easy-to-use two-part needle guide system which provides a fine degree of control for regional anesthesia procedures.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 1A shows an example of a variable-angle style needle guide system having a guiding component set to an angle $\theta_1$.

FIG. 1B shows an example of a variable-angle style needle guide system having a guiding component set to an angle $\theta_2$.

DETAILED DESCRIPTION

Figure 2:
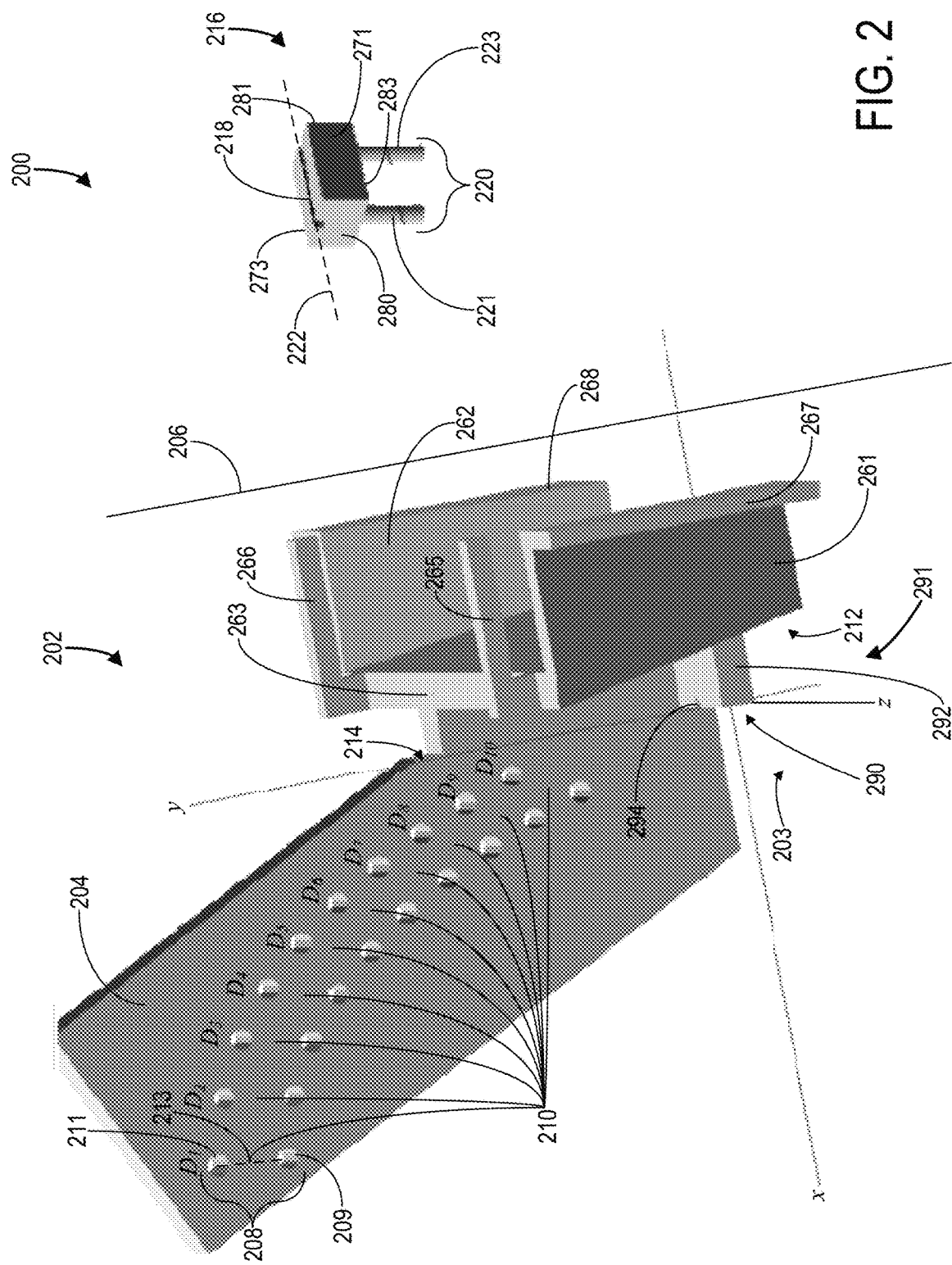
FIG. 2 shows an example needle guide system in accordance with the disclosure.

The following description is directed to a retreating stop ultrasound needle guide system which includes a guiding component which can be positioned at different locations and angles on an ultrasound mounting component thereby providing a fine degree of control for regional anesthesia procedures, for example. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents. The description may use the terms "embodiment" or "embodiments," which may each refer to one or more of the same or different embodiments. Furthermore, the terms "comprising," "including," "having," and the like, as used with respect to embodiments, are synonymous.

Ultrasound coupled needle guides are instruments that guide a needle to a particular position in a patient's tissue and therefore may be described in terms of their accuracy, precision, and measurement resolution. Accuracy generally denotes a system's degree of closeness to a true value; precision refers to the ability for repeated measurements to obtain the same value, and measurement resolution refers to the ability of the instrument to make fine distinctions in measurements. For example, if one considers two hypothetical needle guides designed to position a needle 1 cm in the patient's tissue, their accuracy would refer to how close an average of repeated measurements would be to 1 cm, precision would refer to the spread of values during repeated measurements, and measurement resolution would refer to the distance to the neighboring settings on the needle guide.

The accuracy, precision, and measurement resolution of needle placement when using needle guides is of obvious importance to the clinician. While some anatomic targets, such as the internal jugular vein, are relatively large and therefore will tolerate guides that lack accuracy, precision, or resolution, procedures that target small structures or are near sensitive tissue are less forgiving.

For in-plane needle guides, the needle can be visualized throughout its trajectory to the target, and the clinician may dynamically correct for any shortcomings in the needle guide, or may choose to not use any needle guide at all. However, for out-of-plane approaches, the needle is not visible until it intersects the plane of the ultrasound image, making needle guides much more useful and the characteristics of the needle guide more important.

There are a number of anesthetic procedures that are difficult to perform using an in-plane technique but nonetheless could benefit from ultrasound guidance. These include paravertebral blocks and lumbar plexus blocks. Ultrasound approaches have been described for both of these blocks using an in-plane approach; however, due to the depth, presence of bony obstructions, and presence of other vital structures such as the lung, many clinicians find these blocks difficult to perform using an in-plane technique. In-plane techniques using needle guides have also been described for lumbar epidural placement however, with such in-plane techniques the size of the ultrasound probe and the altered needle trajectory can cause practical difficulties.

The accuracy and precision of a needle guide depend upon a variety of factors, including manufacturing tolerances, flexing of the needle as it passes through tissue, rigidity of the needle guide, etc. The measurement resolution of the guide, however, is largely a function of the specific design of the needle guide. In some approaches, variable-angle style needle guides are used to change the selected depth by changing the angle at which the needle penetrates the skin.

For example, FIG. 1 shows an example variable-angle style needle guide system 100 with an adjustable angle needle guiding component 102 coupled to a mounting component 104 which can be attached to a distal end of an ultrasound probe. In FIG. 1A the angle of the guiding component 102 is positioned at a first angle $\theta_1$ relative to an ultrasound probe axis 110 so that when a needle 108 with a hub 106 is inserted into the guiding component, the needle 108 forms first angle $\theta_1$ relative to ultrasound axis 110. FIG. 1B shows the guiding component 102 positioned at a second angle $\theta_2$ less than first angle $\theta_1$, relative to an ultrasound probe axis 110 so that when needle 108 with hub 106 is inserted into the guiding component, the needle 108 forms second angle $\theta_2$ relative to ultrasound axis 110. In this example, when the guiding component 102 is adjusted to different angles, the needle 108 may enter the tissue of a patient at different entry points. For example, if a plane of the skin of a patient is at a position 112, then when the guiding component is positioned at first angle $\theta_1$ as shown in FIG. 1A, the needle would enter the skin at the point 114; whereas when the guiding component is positioned at second angle $\theta_2$ as shown in FIG. 1B, the needle would enter the skin at the point 116 different from point 114. At these different positions, when the needle 108 is fully inserted into the guiding component 102 so that the hub 106 interfaces with the guiding component 102, the tip 118 of the needle 108 may be located at positions offset from the axis 110 of the ultrasound beam.

Variable angle style needle guides, such as shown in FIG. 1, may have a limited number of depths and angles available, making them unsuitable for the fine degree of control needed for regional anesthesia. Further, regional anesthesia procedures using such variable angle style needle guides may be difficult to perform using in-plane ultrasound needle guide techniques due to the desired needle depth, presence of anatomical obstructions, the size/geometry of the ultrasound probe and the altered needle trajectory created, and the steep angle of needle entry, for example. Further still, since in such variable angle approaches the needle may enter the tissue of a patient at different entry points, accuracy of needle placement may be reduced. Additionally, since the tip of the fully inserted needle may be located at positions offset from the ultrasound beam in such approaches, a needle guide operator may be unable to view the final location of the needle via the ultrasound image thereby further reducing accuracy of needle placement.

In order to address these issues, a retreating stop ultrasound needle guide system is described. As described in more detail below, such a retreating stop ultrasound needle guide system may include a guiding component which can be positioned at different locations and angles on a mounting component, where the mounting component can be coupled to a distal end of an ultrasound probe. When positioned at the different locations and angles on the mounting component, the guiding component can guide a needle through the skin of a patient at a constant point and when the needle is advanced so that a hub of the needle reaches a stop of the guiding component, a tip of the needle is positioned directly underneath the ultrasound at a pre-selected depth.

FIG. 2 shows an example needle guide system 200 which comprises two parts, one of which attaches to the ultrasound (mounting component 202), and one of which provides a groove or channel through which a needle can be inserted (guiding component 216). Needle guide system 200 may be used for out-of-plane ultrasound needle placement where the needle is not visible until it intersects a plane or axis 206 of the ultrasound image. The mounting component 202 may be easily attached and detached from an ultrasound probe via a clip 212 before, during, or after a regional anesthesia procedure and the guiding component 216 may be easily attached and detached at different locations 210 on the mounting component 204 before, during, or after a regional anesthesia procedure.

The needle guide system 200 may be manufactured in any suitable manner and may be composed of any suitable materials or combinations of materials. As one example, the mounting component 202 and the guiding component 216 may be manufactured using injection molding, e.g., based on CAD drawings.

The mounting component 202 comprises a planar mounting surface 204 offset from an ultrasound probe axis 206. The mounting component 202 further includes a clip 212 positioned on a side 214 of the mounting surface 204 adjacent to the probe axis 206. The clip is configured to engage with a distal end of an ultrasound probe so that the probe axis 206 corresponds to an ultrasound beam or plane of the ultrasound probe. In particular, when the mounting component 202 is coupled to a distal end of an ultrasound probe, the mounting surface 204 may be positioned substantially perpendicular to the ultrasound probe in substantially the same plane as the ultrasound probe axis 206.

The clip 212 may have any suitable form configured to engage with features on a distal end of an ultrasound probe. As one example, as shown in FIG. 2, the clip may comprise two opposing tabs 261 and 262 extending from a back wall 263 adjacent to side 214 of mounting surface 204. An outwardly extending lip 267 may be included at a distal end of tab 261 and an outwardly extending lip 268 may be included at a distal end of tab 262. Further, two protrusions 265 and 266 may extend from a top surface of the back wall 263. These features of the clip may be configured to engage with complementary features on the distal end of an ultrasound probe, e.g., as shown in FIG. 6 described below.

The planar mounting surface 204 includes a slot, e.g., slot 208, at each of a plurality of different predetermined locations 210 on the mounting surface. Each of the plurality of different predetermined locations 210 on the mounting surface corresponds to a different predetermined depth along the probe axis 206 below the plane 203 positioned below and perpendicular to the mounting surface. Each slot in mounting surface 204 may take any suitable form and may be configured to mate with a corresponding tab 220 on the guiding component 216 so that the guiding component 216 is releasably coupled to the mounting surface at the location associated with that slot and is held in a fixed position relative to the planar mounting surface at that location.

In some examples, each slot, e.g., slot 208, at each of the plurality of different predetermined locations 210 on the mounting surface may comprises a pair of apertures or holes, e.g., slot 208 may comprises a pair of apertures 209 and 211. In this way, in some examples an array of apertures or holes may be included on mounting surface 204. In particular, each slot 208 corresponds to a particular location on the mounting surface at each of the different predetermined locations 210. When each slot comprises a pair of apertures, the location of that slot may correspond to a midpoint between the apertures in the pair of apertures. For example, the location of slot 208 may correspond to midpoint 213 positioned between apertures 211 and 213 comprising slot 208. In this example, the tab 220 on guiding component 216 may comprise a pair of rods or projections 221 and 223 configured to mate with each pair of apertures. For example, projection 221 may be configured to mate with aperture 208 and projection 223 may be configured to mate with aperture 211 when tab 220 is coupled to slot 208 at location 213 on mounting surface 204. It should be understood that the example slots and tabs described above are provided by way of example and other types of slots and tabs are contemplated. For example, each slot may comprise a rectangular or hexagonal aperture and the tab may comprise a rectangular or hexagonal protrusion configured to be inserted into the rectangular or hexagonal aperture in the mounting surface to hold the guiding component in a fixed position relative to the mounting surface.

The guiding component 216 includes a linear channel 218 extending therethrough which is sized to receive a needle but preclude advancement of the needle through the linear channel beyond a hub of the needle. The guiding component 216 may comprise two opposing sides 271 and 273 parallel to channel 218, two opposing faces 280 and 281 perpendicular to channel 218, and a bottom surface 283 from which the tab 220 extends. The linear channel 218 through guiding component 216 may take any suitable form, e.g., the linear channel may be a linear groove or a cylindrical orifice with a constant diameter extending through the body of the guiding component from back face 281 to front face 280 in a direction parallel to opposing sides 271 and 273.

In some examples, mounting component 202 may include a needle entry point guide element 290 extending from the mounting surface 204 adjacent to a bottom side 291 of the mounting surface 204. For example, as shown in FIG. 2, the needle entry point guide element 290 may comprise a block 292 extending perpendicularly from the mounting surface 204 near the bottom side 291 of the mounting surface 204. The block 292 may include a divot or notch 294 configured to hold a needle in place to direct the needle to a common needle entry point in the skin of a patient, e.g., point 308 described below.

The tab 220 included on guiding component 216 is configured to separately and releasably engage with each slot at each of the plurality of different predetermined locations 210 on the mounting surface to hold the guiding component in a fixed position relative to the planar mounting surface at that location. For example, as remarked above, the tab 220 of the guiding component 216 may comprise a pair of projections 221 and 223 configured to mate with each pair of apertures at each of the different locations 210 on mounting surface 204.

As remarked above, each slot on mounting surface 204 corresponds to a different predetermined depth along the probe axis 206 below the plane 203 positioned below and perpendicular to the mounting surface. Thus, in some examples, indicia, markings, or labels, e.g., the indicia $D_1$ through $D_{10}$ shown on FIG. 2, may be included on mounting surface 204 adjacent to each predetermined location indicating the depth corresponding to that location. The indicia may be included on mounting surface 204 in any suitable way, e.g., indicia may be printed onto the surface, attached to the surface via an adhesive, engraved into the surface, color-coded on the surface, etc. For example, a marking $D_1$ is shown in FIG. 2 on surface 204 adjacent to slot 208 indicating that the location 213 associated with slot 208 corresponds to a depth $D_1$ along the probe axis 206 below the plane 203 positioned below and perpendicular to the mounting surface. In particular, each slot in mounting surface 204 may be labeled with a particular depth, or labeled with a suitable indication of the particular depth, and positioned such that when the tab 220 of the guiding component 216 is inserted into the slot, advancing a needle through the channel 218 of the guiding component 216 to the hub of the needle will position the needle tip to a depth in the center of the ultrasound beam designated by the labels on the mounting surface.

Instead of changing only the angle of needle insertion, a retreating stop needle guide, such as shown in FIG. 2, moves the position and angle of a needle stop, i.e., the guiding component, to guide a needle to a particular location. The retreating stop needle guide could have the slots in a variety of configurations across the mounting surface 204. A simple example design would keep the needle trajectory at a constant angle, and move the slots upward along the mounting surface in a vertical line to change the depth. However, there are several drawbacks to this simple approach. For example, in such a simple approach, keeping the angle constant may limit either the minimum (if a steep angle is chosen) or maximum (if a shallow angle is chosen) depth that can be achieved. Further, in such a simple approach, the point at which the needle penetrates the skin may change with the selected depth, moving further away with a deeper setting, making the guide less useful for blocks that require a steep trajectory, for example.

In order to address these issues, the locations of the slots on the mounting surface may be selected so that when positioned at the different locations 210 on the mounting component 204, the guiding component 216 can guide a needle through the skin of a patient at a constant point and when the needle is advanced so that a hub of the needle reaches a stop of the guiding component, a tip of the needle is positioned directly underneath the ultrasound at a preselected depth. Such an approach may ensure that the tip of the needle intersects the plane of the ultrasound beam at exactly the desired depth and since the needle penetrates the skin at a constant point in this approach, the guide may show the operator where to penetrate the skin. This can make the angle of entry more accurate than if it was determined only by the needle stop, for example.

In order to ensure that the needle penetrates the skin at a constant point and the tip of the needle intersects the plane of the ultrasound beam at exactly the desired depth, the predetermined locations 210 may be selected based on a mathematical formula in order to simultaneously adjust both the angle and the depth of the guiding component 216 to deliver the tip of a needle at a desired location.

Figure 3:
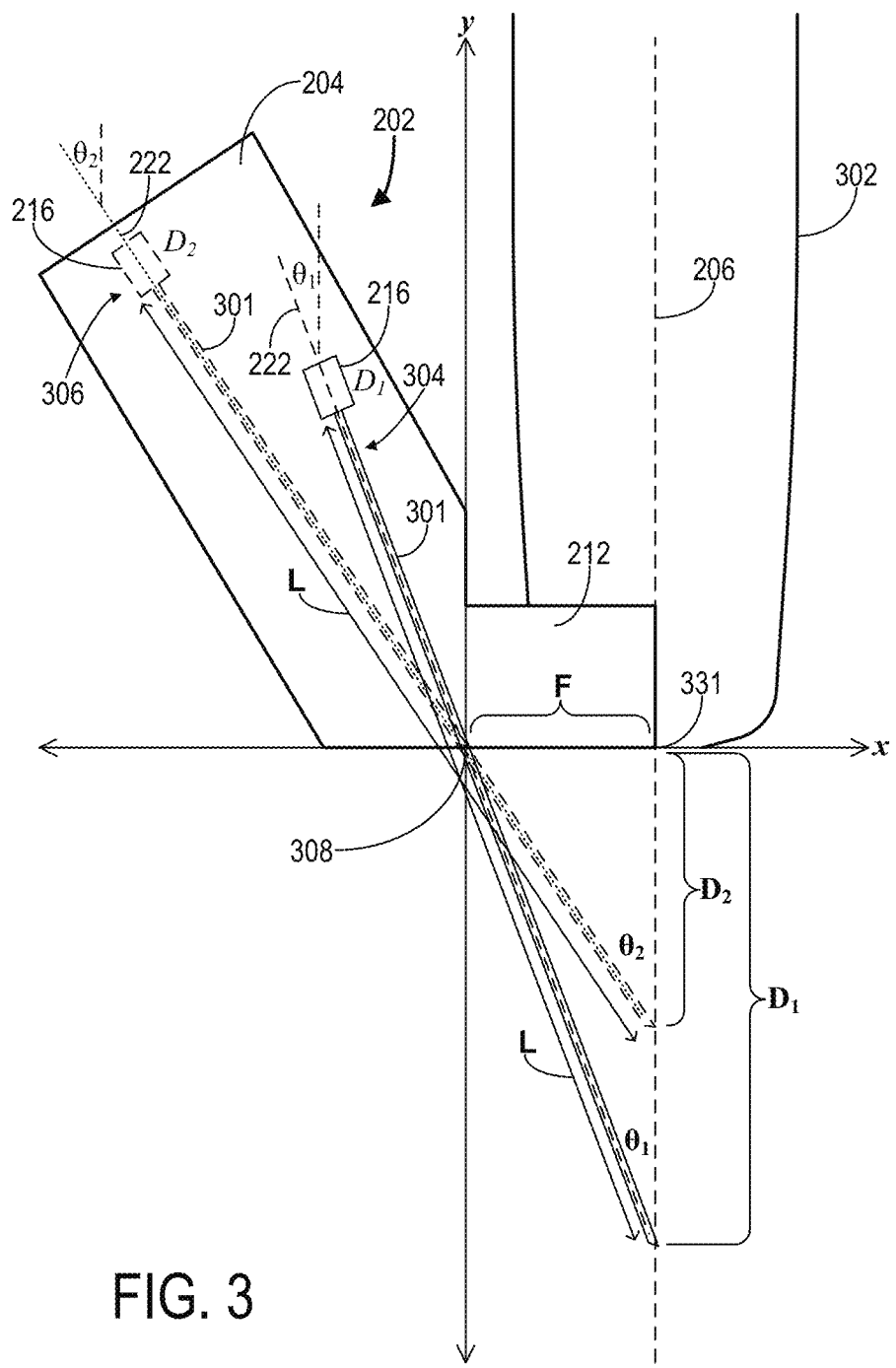
FIG. 3 shows example needle guide dimensions in accordance with the disclosure.

For example, FIG. 3 shows example needle guide dimensions and geometry to illustrate an example selection of predetermined slot locations 210 on the mounting surface 204. Like-numbered elements shown in FIG. 3 correspond to like-numbered elements shown in FIG. 2 described above. It should be understood that the example coordinates for the predetermined locations 210 on mounting surface 204 are given for illustrative purposes and should not be taken in a limiting sense. In particular, any suitable coordinates based on any suitable constrains may be used to describe the different locations of the slots on mounting surface 204.

FIG. 3 shows mounting component 202 coupled to a distal end of an ultrasound probe 302 via a clip 212 attached to mounting surface 204. An ultrasound probe axis 206 may correspond to a plane of an ultrasound beam of the ultrasound probe. A coordinate system comprising an x-axis and a y-axis is shown in FIG. 3. FIG. 3 shows a guiding component 216 coupled to the mounting surface 204 at two different example positions indicated at 304 and at 306 in FIG. 3. FIG. 3 also shows a needle 301 fully inserted through the linear channel of the guiding component 216 such that a hub of the needle 301 interfaces with the guiding component to preclude any further advancement of the needle through the linear channel. The length of the fully inserted needle is labeled "L" in FIG. 3.

With reference to FIGS. 2 and 3, when the guiding component 216 is coupled to different locations in the plurality of predetermined locations 210 on mounting surface 204, the angle of a central axis 222 extending through the linear channel of the guiding component takes on different values. For example, when the guiding component 216 is coupled to the mounting surface at a first position 304 shown in FIG. 3, the central axis 222 forms an angle $\theta_1$ relative to the probe axis 206; and when the guiding component 216 is coupled to the mounting surface at a second different position 306 shown in FIG. 3, the central axis 222 forms an different angle $\theta_2$ relative to the probe axis 206.

The predetermined locations 210 may be selected so that for each location of the plurality of different predetermined locations 210 on the mounting surface 204, when the tab 220 of the guiding component 216 is engaged with the slot at that location, the following conditions are met: (1) the central axis 222 extending through the linear channel 218 of the guiding component 216 is substantially parallel to the planar mounting surface 204 and offset from the planar mounting surface 204 by substantially the same distance, (2) the central axis 222 intersects substantially the same point 308 in a plane 203 positioned below and perpendicular to the mounting surface 204, and (3) the distance between the guiding component 216 and the probe axis 206 along the central axis 222 is the substantially the same distance. For example, for each location of the plurality of different predetermined locations 210 on the mounting surface 204, when the tab 220 of the guiding component 216 is engaged with the slot at that location, the distance between the guiding component 216 and the probe axis 206 along the central axis 22 may be substantially the same as the length, L, as the fully inserted needle 301. Further, the common intersection point 308 may correspond to the intersection of the x-axis and y-axis shown in FIG. 3 which may, in turn, correspond to a fixed tissue insertion point of the needle when deployed through the guiding component 216 at each of the different locations 210 on the mounting surface 204.

The coordinate system shown in FIG. 3 has an origin at the common intersection point 308 where the central axis 222 of the linear channel 218 of the guiding component 216 intersects the plane positioned below and perpendicular to the mounting surface 204 when the tab 220 of the guiding component 216 is engaged with the slot at each location of the plurality of different predetermined locations 210 on the mounting surface. Further, the x-axis extends through the origin 308 in the plane 203 positioned below and perpendicular to the mounting surface 204 and parallel to the plane of the mounting surface 204, and the y-axis extends through the origin 308 parallel to the probe axis 206 and parallel to the plane of the mounting surface 204. In FIG. 3, F refers to the distance between the origin 308 and the point of intersection 331 of the x-axis with the probe axis 206, and $D_1$ and $D_2$ are example predetermined depths D along the probe axis 206 below the plane 203 positioned below and perpendicular to the mounting surface 204.

As an example, the plurality of different predetermined locations 210 on the mounting surface may be defined by coordinates (x, y) in the coordinate system shown in FIG. 3 and described above, where the coordinates (x, y) are defined by the following equations:

$$x = -\left(\sqrt{\frac{L^2}{\frac{D^2}{F^2}+1}} - F\right), y = \sqrt{\frac{L^2}{\left(\frac{F^2}{D^2}+1\right)}} - D,$$

where F is the distance between the origin 308 and the point of intersection 331 of the x-axis with the probe axis 206, L is the length of the needle, and D is a predetermined depth along the probe axis. Further, when the tab 220 of the guiding component 216 is engaged with a slot at a location in the plurality of different predetermined locations 210 on the mounting surface, the angle, θ, formed between the central axis 222 extending through the linear channel 218 of the guiding component 216 and the probe axis 206 may be defined by the following equation:

$\tan θ = F/D$, where D is the predetermined depth which corresponds to the location of the slot.

For example, with reference to FIG. 3, when the guiding component 216 is coupled to the mounting surface 204 at the position shown at 304, the coordinates (x,y) of the location of the guiding component 216 on the mounting surface may be described as:

$$x = -\left(\sqrt{\frac{L^2}{\frac{D_1^2}{F^2}+1}} - F\right), y = \sqrt{\frac{L^2}{\left(\frac{F^2}{D_1^2}+1\right)}} - D_1,$$

and the angle of the central axis 222 relative to the probe axis 206 may be defined as:

$\tan θ_1 = F/D_1$.

Likewise, when the guiding component 216 is coupled to the mounting surface 204 at the position shown at 306, the coordinates (x,y) of the location of the guiding component 216 on the mounting surface may be described as:

$$x = -\left(\sqrt{\frac{L^2}{\frac{D_2^2}{F^2}+1}} - F\right), y = \sqrt{\frac{L^2}{\left(\frac{F^2}{D_2^2}+1\right)}} - D_2,$$

and the angle of the central axis 222 relative to the probe axis 206 may be defined as:

$\tan θ_2 = F/D_2$.

The predetermined depths D along the probe axis 206 below the plane 203 positioned below and perpendicular to the mounting surface 204 may be preselected to have any suitable resolution and intervals. For example, distances along the probe axis between each depth in the predetermined depths selected to be in a range of approximately 2-3 millimeters. As such, any suitable number of different slot locations 210 on the mounting surface 204 may be used to achieve a desired depth resolution and interval. For example, as shown in FIG. 2, ten different locations 210 may be chosen to achieve a desired needle depth resolution.

Figure 4:
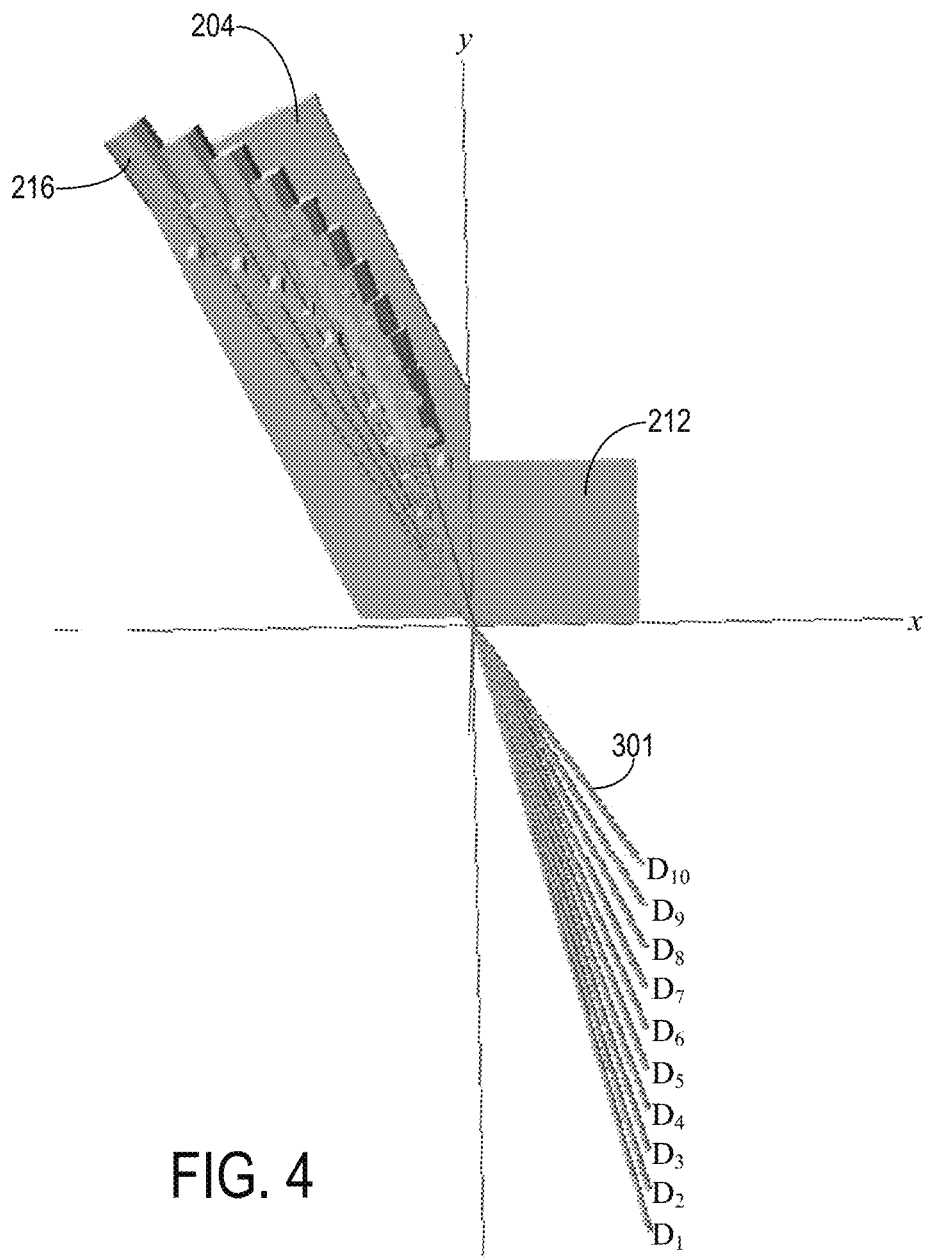
FIG. 4 shows an example needle guide with a needle inserted at various depths in accordance with the disclosure.

FIG. 4 shows an example model of a needle guide with a needle inserted at various depths. In the example shown in FIG. 4, there are ten different predetermined slot locations 210 on mounting surface 204 to which the guiding component 216 may be coupled in order to achieve 10 different depths along the probe axis, $D_1$ through $D_{10}$, at which the tip of the needle 301 intersects the ultrasound plane. As shown in FIG. 4, the predetermined depths may occur at regular intervals as determined by the desired measurement resolution.

Figure 5:
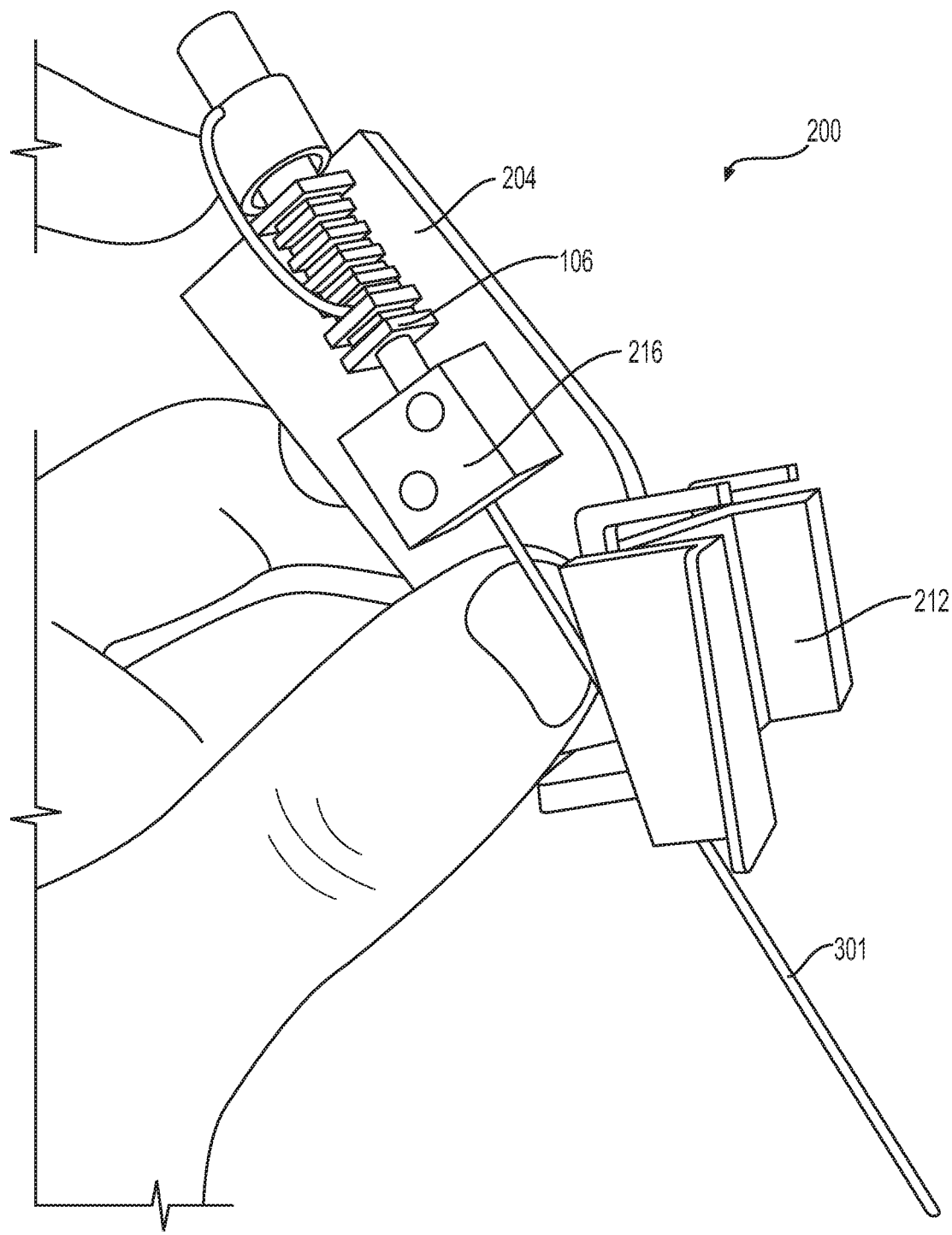
FIG. 5 shows an example embodiment of a needle guide system in accordance with the disclosure.
Figure 6A:
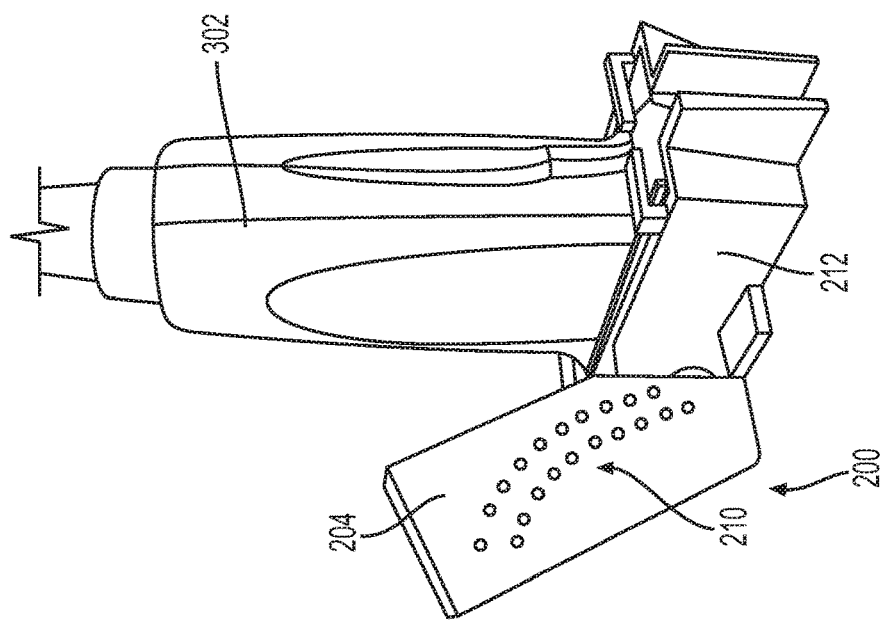
FIG. 6A shows an example of a variable-angle needle guide system coupled to an ultrasound probe.
Figure 6B:
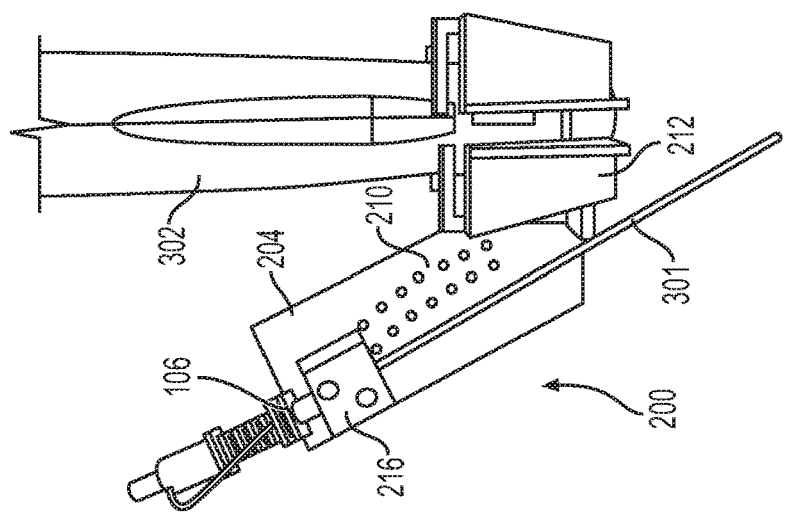
FIG. 6B shows an example of a variable-angle needle guide system having a needle advanced to an operator-selected depth.
Figure 6C:
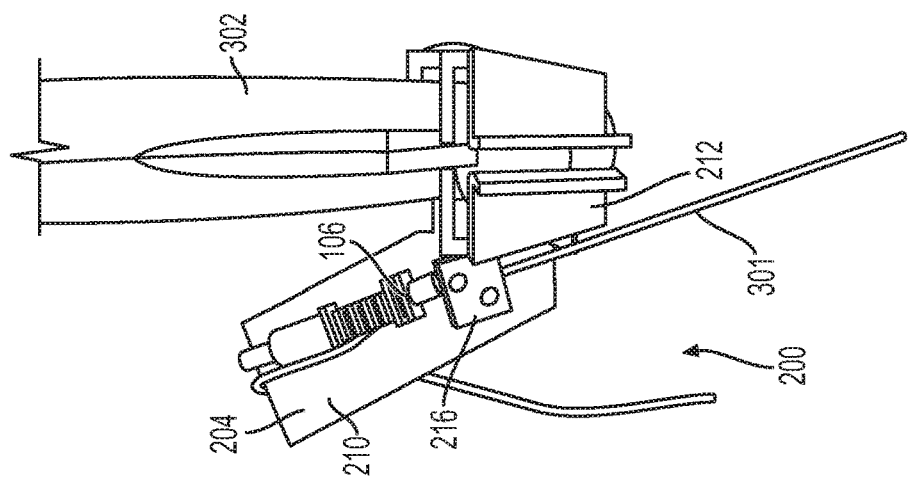
FIG. 6C shows an example of a needle advanced to a deeper operator-selected depth than the depth shown in FIG. 6B.

FIG. 5 shows an example embodiment of a needle guide system 200 in accordance with the disclosure. Like-numbered elements shown in FIG. 5 correspond to like-numbered elements shown in the previous figures and described above. In FIG. 5, a human hand is shown illustrating the relative scale of various dimensions of components of the needle guide system 200. FIG. 5 shows a needle 301 fully inserted through a guiding component 216 coupled to the mounting surface at a selected location. FIG. 6 shows an example embodiment of a needle guide system 200 fabricated via 3-D printing and coupled to an ultrasound probe 302. Like-numbered elements shown in FIG. 6 correspond to like-numbered elements shown in the previous figures and described above. In particular, FIG. 6A shows the needle guide attached to an ultrasound head, FIG. 6B shows the guide after the operator has selected a depth, inserted the guiding component, i.e., depth stop, and advanced the needle, and FIG. 6C shows the guide with a deeper depth selected.

The above-described retreating stop needle guide is able to offer increased measurement resolution when compared to the variable angle needle guide shown in FIG. 1 because both the angle of needle entry and the depth of the needle are changed when changing settings. For example, consider a retreating stop needle guide with settings that are spaced 2.5 mm apart such that the pair of apertures or holes in the mounting surface 204 for one setting is 2.5 mm above or below the previous set, as well as slightly rotated. Assuming that the radius of the apertures is less than 2.5 mm, this can be easily fabricated without the apertures overlapping. In contrast, variable angle needle guides rotate the guiding structure without translating it, causing the needle tracks to overlap when the measurement resolution is too small.

Figure 7:
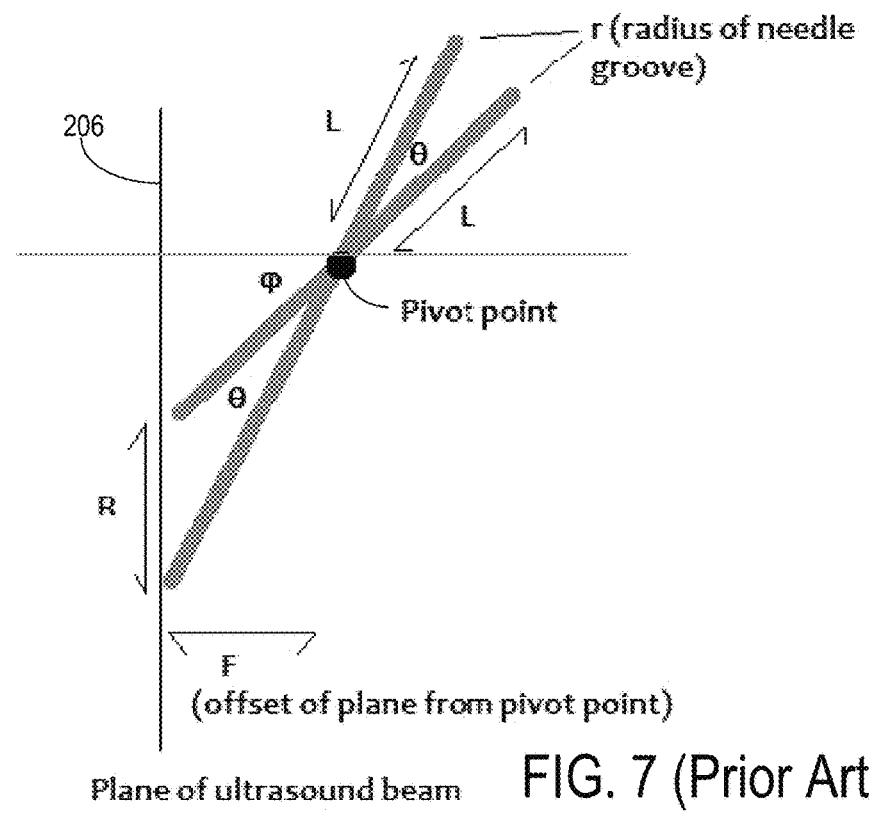
FIG. 7 shows a schematic illustration of an example prior art variable angle needle guide.

For example, FIG. 7 shows an example of two possible needle paths in a variable angle needle guide, such as the variable angle needle guide shown in FIG. 1. In FIG. 7, L refers to the length from the pivot point of the needle to the entry hole in the needle guide, θ refers to the change in angle between two depth settings, r refers to the radius of the needle guide holes, F refers to the offset between the pivot point and the plane of the ultrasound, and φ is the angle between the needle and the perpendicular to the ultrasound beam plane. In this example, the minimum angular change that keeps the needle guide paths distinct is given by the formula: $Lθ<r$. The minimum acceptable angular change can then be used to calculate the measurement resolution of the guide. Based on the geometry shown in FIG. 7, the formula for measurement resolution is $R=F\ (\tan(φ+θ)-\tan(φ))$. Though the measurement resolution of a variable angle needle guide may be a more complex function of the needle radius, the offsets from the pivot point, and the target depth, most variable angle needle guides offer a measurement resolution of approximately 1 cm which is significantly lower that resolutions which may be achieved using the retreating stop needle guide described herein.

Though, the problem of overlapping needle guide paths in variable angle needle guides may be addressed by making the needle guide path detachable, e.g., by included a variety of different angles in a kit, and allowing the operator to choose the desired angle and depth, such an approach may rely on a number of different detachable components thereby potentially increasing complexities of use. For example, a kit with measurement resolution of 2.5 mm and selectable depths between 2 and 6 cm may use 17 different detachable components, making this option undesirable. Another advantage of retreating stop compared to variable angle needle guides is that the needle cannot be advanced beyond the plane of the ultrasound. Variable angle needle guides, if used out of plane, may require the operator to see the tip of the needle appear in the ultrasound image, which may be difficult for smaller needles at greater depths.

Figure 8:
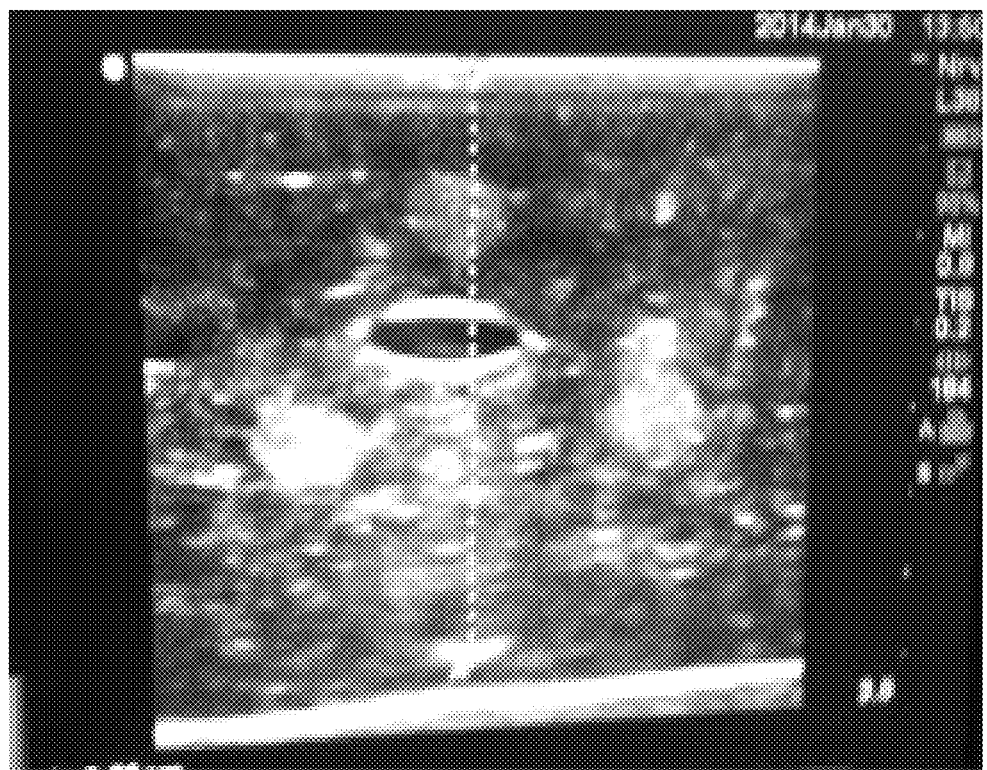
FIG. 8 shows an ultrasound image during a simulated application of a needle guide in accordance with the disclosure.

The retreating stop needle guide shown in FIGS. 5 and 6 was tested for accuracy. In particular, the retreating stop needle guide was mounted on a linear probe for a portable ultrasound (manufactured by Sono-Site). A 100 mm, 21 gauge SONOPLEX STIM cannula manufactured by PAJUNK Medical Systems L.P. was loaded into the needle guide, and inserted into an ultrasound training model (manufactured by Blue Phantom). To ensure good contact between the ultrasound training model and the ultrasound probe, the needle guide was mounted 2 mm above the tip of the probe instead of flush with the tip; for this reason all measurements were shifted by 2 mm upward, this was then corrected for after the measurement. The needle tip was identified by ultrasound (Sono-Site) and the depth to the needle tip measured using a built in calipers function. FIG. 8 shows an ultrasound image during this simulated application of the needle guide.

In the simulation, the depth to the needle tip was measured at settings that corresponded to 3.5, 4.0, and 4.5 cm. At greater depths, the needle tip became increasingly difficult to identify, and when it was identified it was often elongated, making the measurement process difficult. Because of this, no measurements greater than 4.5 cm were attempted. The measurements were repeated five times to assess the accuracy and reproducibility of the guide. The results of the simulation are shown in Table 1 which shows a comparison between depth settings and average measured depths by the ultrasound.

TABLE 1

| Depth Setting (cm) | 3.500 | 4.000 | 4.500 |
|---|---|---|---|
| Average Measured Depth (cm) | 3.520 | 4.044 | 4.526 |
| Standard Deviation (cm) | 0.029 | 0.049 | 0.048 |

As demonstrated by the simulation results, the retreating stop needle guide demonstrated relatively good accuracy in achieving the desired depths and may be reliably used in anesthetic procedures, e.g., paravertebral blocks and lumbar plexus blocks, which may be difficult to perform using in-plane ultrasound needle guide techniques. In such an approach, an increased number of depths and angles may be used so that increased accuracy, precision, and measurement resolution may be achieved.

It is to be understood that the configurations and/or approaches described herein are exemplary in nature, and that these specific embodiments or examples are not to be considered in a limiting sense, because numerous variations are possible. The subject matter of the present disclosure includes all novel and nonobvious combinations and sub-combinations of the various processes, systems and configurations, and other features, functions, acts, and/or properties disclosed herein, as well as any and all equivalents thereof.

The invention claimed is:

1. A needle guide system for engagement with an ultrasound probe having a probe axis, the needle guide system comprising:
   a mounting component, the mounting component comprising:
   a planar mounting surface including a slot at each of a plurality of different predetermined locations on the planar mounting surface; and
   a clip positioned on a side of the planar mounting surface, the clip being configured to engage with the distal end of the ultrasound probe and, when engaged with the distal end of the ultrasound probe, position the planar mounting surface adjacent to the probe axis;
   a guiding component with a linear channel extending therethrough to guide a needle having a length, the guiding component including a tab configured to separately and releasably engage with each slot at each of the plurality of different predetermined locations on the planar mounting surface to hold the guiding component in a fixed position relative to the planar mounting surface at that location;
   wherein, for each location of the plurality of different predetermined locations on the planar mounting surface, when the tab of the guiding component is engaged with the slot at that location:
   a) a central axis extends through the linear channel of the guiding component substantially parallel to the planar mounting surface and offset from the planar mounting surface by substantially a same distance;
   b) the central axis intersects substantially a same point in a plane positioned below and perpendicular to the planar mounting surface;
   c) the distance between the guiding component and the probe axis along the central axis is substantially the same distance; and
   d) when the needle is fully inserted through the guiding component, the length of the needle reaches a different depth along the probe axis.

2. The system of claim 1, wherein the clip is configured to engage with a distal end of the ultrasound probe and the probe axis corresponds to an ultrasound beam of the ultrasound probe.

3. The system of claim 1, wherein the needle has a hub and the linear channel is sized to receive the needle and preclude advancement of the needle through the linear channel beyond the hub of the needle.

4. The system of claim 1, wherein each slot at each of the plurality of different predetermined locations on the planar mounting surface comprises a pair of apertures and wherein the tab of the guiding component comprises a pair of projections configured to mate with each pair of apertures.

5. The system of claim 1, wherein the plurality of different predetermined locations on the planar mounting surface are defined by coordinates (x, y) in a coordinate system with an origin at the same point where the central axis of the linear channel of the guiding component intersects the plane positioned below and perpendicular to the planar mounting surface when the tab of the guiding component is engaged with the slot at a location of the plurality of different predetermined locations on the planar mounting surface, an x-axis extending through the origin in the plane positioned below and perpendicular to the planar mounting surface and parallel to the planar mounting surface, and a y-axis extending through the origin parallel to the probe axis and parallel to the plane of the planar mounting surface, and where the coordinates (x, y) are defined by the following equations:

$$x = -\left(\sqrt{\frac{L^2}{\left(\frac{D^2}{F^2}+1\right)}} - F\right), y = \left(\sqrt{\frac{L^2}{\left(\frac{F^2}{D^2}+1\right)}} - D\right)$$

where F is the distance between the origin and a point of intersection of the x-axis with the probe axis, L is the length of the needle guided therethrough, and D is a predetermined depth along the probe axis.

6. The system of claim 5, wherein, when the tab of the guiding component is engaged with the slot at a location in the plurality of different predetermined locations on the planar mounting surface, the angle, θ, formed between the central axis extending through the linear channel of the guiding component and the probe axis is defined by the following equation:

$\tan \theta = F/D$, where D is the predetermined different depth which corresponds to the location of the slot.

7. The system of claim 6, wherein each slot at each of the plurality of different predetermined locations on the planar mounting surface comprises a pair of apertures and wherein the location of the slot is defined as the midpoint between the apertures in each pair of apertures, and wherein the tab of the guiding component comprises a pair of projections configured to mate with the pair of apertures.

8. The system of claim 1, wherein each of the predetermined locations of the plurality of different predetermined locations on the planar mounting surface correspond to a predetermined different depth along the probe axis below the plane positioned below and perpendicular to the planar mounting surface and wherein the planar mounting surface includes an indicium adjacent to each predetermined location indicating the different depth corresponding to that location, such that, when the tab of the guiding component is engaged at a predetermined location on the planar mounting surface, the length of a needle fully inserted through the guiding component reaches the depth along the probe axis corresponding to the indicium adjacent the predetermined location on the planar mounting surface.

9. The system of claim 8 wherein each indicium corresponds to a predetermined different depth along the probe axis in predetermined different depth intervals of approximately 2-3 millimeters.

10. The system of claim 1, further comprising a needle entry point guide element extending from a bottom side of the planar mounting surface and including a notch to hold the needle in place to direct the needle to the same point where the central axis of the linear channel of the guiding component intersects the plane positioned below and perpendicular to the planar mounting surface when the tab of the guiding component is engaged with the slot at a location of the plurality of different predetermined locations on the planar mounting surface.

11. An out-of-plane ultrasound needle guide for engagement with an ultrasound probe having a probe axis corresponding to an ultrasound beam of the ultrasound probe, the needle guide comprising:

a mounting component, the mounting component comprising:
a planar mounting surface, the planar mounting surface including a slot at each of a plurality of different predetermined locations on the planar mounting surface; and
a clip positioned on a side of the planar mounting surface the clip being configured to engage with the distal end of the ultrasound probe having a probe axis and, when engaged with the distal end of the ultrasound probe, position the planar mounting surface adjacent to the probe axis;
a guiding component with a linear channel extending therethrough to guide a needle having a length, wherein the linear channel is sized to receive the needle and preclude advancement of the needle through the linear channel beyond a hub of the needle, the guiding component including a tab configured to separately and releasably engage with a slot selected from the plurality of different predetermined locations on the planar mounting surface to hold the guiding component in a fixed position relative to the planar mounting surface at that location;
wherein, for each location of the plurality of different predetermined locations on the planar mounting surface, when the tab of the guiding component is engaged with the slot at that location:
a) a central axis extending through the linear channel of the guiding component is substantially parallel to the planar mounting surface and offset from the planar mounting surface by substantially a same distance,
b) the central axis intersects substantially a same point in a plane positioned below and perpendicular to the planar mounting surface,
c) the distance between the guiding component and the probe axis along the central axis is substantially the same as the length of the needle, and
d) when the needle is fully inserted through the guiding component, the length of the needle reaches a different predetermined depth along the probe axis.

12. The needle guide of claim 11, wherein each slot at each of the plurality of different predetermined locations on the planar mounting surface comprises a pair of apertures and wherein the tab of the guiding component comprises a pair of projections configured to mate with each pair of apertures.

13. The needle guide of claim 11, wherein each predetermined location of the plurality of different predetermined locations on the planar mounting surface corresponds to a predetermined different depth along the probe axis below the plane positioned below and perpendicular to the planar mounting surface.

14. The needle guide of claim 13, wherein the planar mounting surface includes indicia adjacent to each predetermined location indicating the different depth corresponding to that location.

15. The needle guide of claim 13, wherein the plurality of different predetermined locations on the planar mounting surface are defined by coordinates (x, y) in a coordinate system with an origin at the same point where the central axis of the linear channel of the guiding component intersects the plane positioned below and perpendicular to the planar mounting surface when the tab of the guiding component is engaged with the slot at a location of the plurality of different predetermined locations on the planar mounting surface, an x-axis extending through the origin in the plane positioned below and perpendicular to the planar mounting surface and parallel to the planar mounting surface, and a y-axis extending through the origin parallel to the probe axis and parallel to the plane of the planar mounting surface, and where the coordinates (x, y) are defined by the following equations:

$$x = -\left(\sqrt{\frac{L^2}{\left(\frac{D^2}{F^2}+1\right)}} - F\right), y = \left(\sqrt{\frac{L^2}{\left(\frac{F^2}{D^2}+1\right)}} - D\right)$$

where F is the distance between the origin and a point of intersection of the x-axis with the probe axis, L is the length of the needle guided therethrough, and D is a predetermined depth along the probe axis, and wherein, when the tab of the guiding component is engaged with the slot at a location in the plurality of different predetermined locations on the planar mounting surface, the angle, θ, formed between the central axis extending through the linear channel of the guiding component and the probe axis is defined by the following equation:

$\tan \theta = F/D$, where D is the predetermined different depth which corresponds to the location of the slot.

* * * * *